United States Patent [19]
Dulebohn

[11] Patent Number: 5,100,410
[45] Date of Patent: Mar. 31, 1992

[54] MEANS AND METHOD FOR FACILITATING FOLDING OF AN INTRAOCULAR LENS

[75] Inventor: David H. Dulebohn, Tonka Bay, Minn.

[73] Assignee: Andrew Tool Co., Inc., Tonka Bay, Minn.

[21] Appl. No.: 647,517

[22] Filed: Jan. 28, 1991

[51] Int. Cl.$^5$ .............................. A61B 17/00
[52] U.S. Cl. ......................... 606/107; 623/6; 206/5.1
[58] Field of Search ............. 623/6; 606/107; 206/5.1, 438

[56] References Cited

U.S. PATENT DOCUMENTS

| | | | |
|---|---|---|---|
| 450,266 | 4/1891 | Truax | 294/992 |
| 1,837,277 | 12/1931 | Lund | 606/110 |
| 4,198,980 | 4/1980 | Clark | 606/107 |
| 4,303,268 | 12/1981 | Davidson | 294/992 |
| 4,325,375 | 4/1982 | Nevyas | 606/207 |
| 4,462,404 | 7/1984 | Schwarz et al. | 606/142 |
| 4,573,998 | 3/1986 | Mazzocco | 623/6 |
| 4,681,102 | 7/1987 | Bartell | 606/107 |
| 4,702,244 | 10/1987 | Mazzocco | 623/6 |
| 4,759,359 | 7/1988 | Willis et al. | 606/107 |
| 4,769,034 | 9/1988 | Poley | 623/6 |
| 4,785,810 | 11/1988 | Baccala et al. | 606/207 |
| 4,791,924 | 12/1988 | Kelman | 128/303 R |
| 4,813,956 | 3/1989 | Gupta | 623/6 |
| 4,813,957 | 3/1989 | McDonald | 623/6 |
| 4,836,201 | 6/1989 | Patton et al. | 623/6 |
| 4,844,065 | 7/1989 | Faulkner | 128/321 |

FOREIGN PATENT DOCUMENTS

WO82/01646  5/1982  PCT Int'l Appl.
2191439A    12/1987  United Kingdom.

OTHER PUBLICATIONS

"Intracameral Lenses Made of Hydrocolloid Acrylates", by Dreifus, Wichterle and Lim, of II. Eye Clinic, Charles University from Sc. oftamologie 16(2), 454–459 (1960) (translation from Czech).

"Folding and Inserting Silicon Intraocular Lens Implants", by Gerald D. Faulkner M.D., *J. Cataract Refract Surf*, vol. 13, Nov. 1987, pp. 678–681.

"Pathologic Findings of an Explanted Silicone Intraocular Lens", by Newman, McIntyre, Apple, Deacon, Popham, and Isenberg; *J Cataract Refract Surg*, vol. 12, May 1986, pp. 292–297.

*Primary Examiner*—Randy C. Shay

[57] ABSTRACT

A system for facilitating folding a soft intraocular lens. A supporting and positioning structure associated with a base or frame presents the lens so that forceps tips are automatically positioned near opposite sides of the lens and maintained in that position. A forming means automatically moves the forceps tips with respect to the lens to fold the optic portion of the lens within the tips. The lens is accurately and reliably folded in the forceps tips to securely grip the lens in a desired position with reduced risk of damage to the optic portion of the lens.

21 Claims, 4 Drawing Sheets

MEANS AND METHOD FOR FACILITATING FOLDING OF AN INTRAOCULAR LENS

BACKGROUND OF THE INVENTION

The replacement of lens of a human eye generally utilizes a surgical procedure whereby an artificial replacement lens is inserted through an incision in the eye. Once inside the eye, the surgeon manipulates the lens into a position where it is then secured. To minimize trauma to the eye, it is most beneficial to minimize the size of the incision through which the lens is inserted.

This type of artificial lens, generally referred to as an intraocular lens, is usually comprised of a circular convex or plano-convex optic portion, with arms called haptics extending from the optic. The haptics are utilized to hold the lens in place.

A practical limitation on how small the incision in the eye can be is the diameter of the optic portion of the lens. Although tissue is somewhat pliable, a slit or incision has to be approximately, at a minimum, the length of the diameter of the lens. One way to avoid this limitation is to manipulate the lens to reduce its cross-sectional diameter before insertion into the eye. An example would be to fold the lens over onto itself. This would reduce the required length of the incision by approximately one half.

The present invention relates to lens insertion and intraocular lens replacement surgery, and in particular, to an improved means and method for folding a lens in preparing it for insertion into the eye. The benefits of one smaller incision are less trauma to the eye.

The concept of folding or rolling a lens prior to insertion is known in the art. See, for example, the following U.S. Pat.:

| Faulkner | 4,844,065 |
| Poley | 4,769,034 |
| Patton | 4,836,201 |
| Mazzocco | 4,702,244 |
| Bartell | 4,681,102 |
| Willis | 4,759,359 |
| Baccala | 4,785,810 |

Patents such as Faulkner, Poley, Willis, and Baccala illustrate how the folding of a lens may be done, or disclose and claim instruments used in association with such folding. Patents such as Patton, Mazzocco and Bartell disclose rather complex instruments and associated hardware for rolling or otherwise manipulating the lens into a smaller cross sectional or diametric-shape.

It has been determined that although the above technology exists in the art, there is room for improvement as to how a lens can be reliably and accurately folded. Intraocular lens replacement is a highly technical and delicate surgery. It deals with replacing a natural part of the eye with an artificial implant. The value of eyesight is immeasurable. Therefore, it is critical that all possible steps be taken to insure the best possible lens replacement and procedures.

Room for improvement exists in the ability of precise, accurate, and reliable folding of lens, if that procedure is used. A surgeon needs to have a good grip on a lens for its insertion. The lens cannot be damaged or scratched. The folding needs to be accomplished quickly and easily. It is insufficient, or at least problematic, for a surgeon to accomplish such delicate and minute folding without some standardized procedure or structure.

Moreover, it is also disadvantageous to utilize complex procedure or methods. Complexity leads to the risk of malfunction or, at a minimum, difficulties in learning the process or structure.

Additionally, the technology regarding the artificial intraocular lenses themselves has advanced. The optic portions of the lenses themselves may be made of several different materials. Some of these materials have characteristics which allow them to provide good optical qualities and durability. Some of the materials, however, are not particularly easy to fold or manipulate. One problem deals with lenses which are made of substances like silicone which are resilient and very deformable. This makes it difficult to maintain a secure grip on the lens when folded as the lens has a tendency to return to its original position. The second problem exists in taking great care to avoid any damage to the lens optic. Any gripping of the lens, especially near the optical center, runs this risk.

The need therefore exists for a means and method of reliably and accurately folding a soft intraocular lens, including those lens optics which are made of a variety of different materials.

It is therefore the principal object of the present invention to provide a means and method for facilitating folding of a foldable intraocular lens which overcomes or improves over the problems and deficiencies in the art.

It is a further object of the present invention to provide a means and method as above described which presents an easy, accurate, and reliable way to fold intraocular lenses.

A still further object of the invention is to provide a means and method as above described which greatly reduces the risk of inaccurate folding and gripping of an intraocular lens.

A still further object of the present invention is to provide a means and method as above described which reduces the risk of damage to an intraocular lens which is folded.

A still further object of the present invention is to provide a means and method as above described which is noncomplex and easy to understand and adopt.

A still further object of the present invention is to provide a means and method as above described which is adaptable to a variety of intraocular lenses.

Another object of the present invention is to provide a means and method as above described which minimizes handling of the lens.

Another object of the present invention is described which minimizes the risk of upside down installation of the lens, as it will always be packaged, presented, and folded within the forceps tip in the correct position.

Another object of the present invention is to provide a means and method as above described which is economical and efficient.

These and other object, features, and advantages of the present invention will become more apparent with references to the accompanying specification and claims.

SUMMARY OF THE INVENTION

The present invention presents a system whereby the surgeon can confidently know that lens can be quickly and accurately folded with forceps, with a minimum risk of damage to the lens. The method involves the steps of positioning and supporting the lens to be folded so that forceps tips can easily and quickly be brought into preselected, desired positions near opposite diametrical sides of the optic portion of the lens. The tips are automatically located in optimal positions to grip the lens when it is folded.

Structure surrounding the tips, and assisting in their placement, can then be moved by manual force to automatically cause the lens to accurately fold in two, and the forceps tips to be maintained in continuous contact with the optic portion of the lens as it is folded. As the tips are held in position, mechanical force is applied to the structure around the tips to urge the tips towards one another. The lens is supported in such a way that its center portion raises, and the structure basically ensures that the lens folds accurately upon itself and the forceps tips reliably grasp and hold the lens in the folded shape without the use of a second pair of forceps or a folding mandrel.

The apparatus according to the invention includes a base, a supporting structure associated with the base for supporting the lens, a positioning structure to position and maintain the forceps tips with respect to the lens, and moveable structure to cause, assist and guide the closing of the forceps tips concurrently with folding of the lens. The lens can basically be automatically folded in half. The forming structure is basically a vise which causes accurate positioning of the forceps tips, and then accurate closing of the tips and folding of the lens in one quick, easy, and accurate step. Once folded by the folder, the lens is removed by the forceps. The forceps does not fold the lens. That is accomplished by the folder.

The invention allows the surgeon to quickly, with only a few steps and with high assurance, fold the lens for insertion into the eye with reduced risk of damage to the lens. This is done with a noncomplex but reliable structure which is also economical and easy to understand and learn.

DETAILED DESCRIPTION OF PREFERRED EMBODIMENT

In order to assist in a better understanding of the invention, a detailed description of preferred embodiments of the same will now be set forth. The description will be made with reference to the accompanying drawings. Reference numbers are utilized in the description and drawings to specify particular parts or locations in the drawings. The same reference numbers will be utilized for the same parts in all the drawings unless otherwise indicated.

Turning to the embodiment shown in FIGS. 1–10, folder 10 includes a frame 12. In turn, frame 12 includes a gripping portion 14 and a supporting portion 16. As can be seen from FIG. 1, frame 12 consists basically of two mirror images along a longitudinal axis. When discussing gripping portion 14 and supporting portion 16, both opposite mirror image sides of each portion are included. It is to be understood that folder 10 not only facilitates the easy and reliable folding of an intraocular lens 18 within the tips 20 of a forceps 22, but also can serve as a storage device for the lens prior to insertion. Still further, it can serve as basically a packaging device whereby the lens 18 can be mounted, secured, and then packaged in mass quantities for shipping to desired locations. As is well within the skill and understanding of those within the art, the entire frame 12, including a lens and a block insert 24, could be secured in place by a rubber band or the like on the supporting portion 16 of frame 12 (see FIG. 3), and then hygienically packaged within plastic packaging, or a box for shipment. This eliminates the step of removing the lens 18 from its container, placing it onto folder 10, and then performing the folding function. Obviously, however, folder 10 could be used in this manner if desired.

Figures 1, 2, 4:
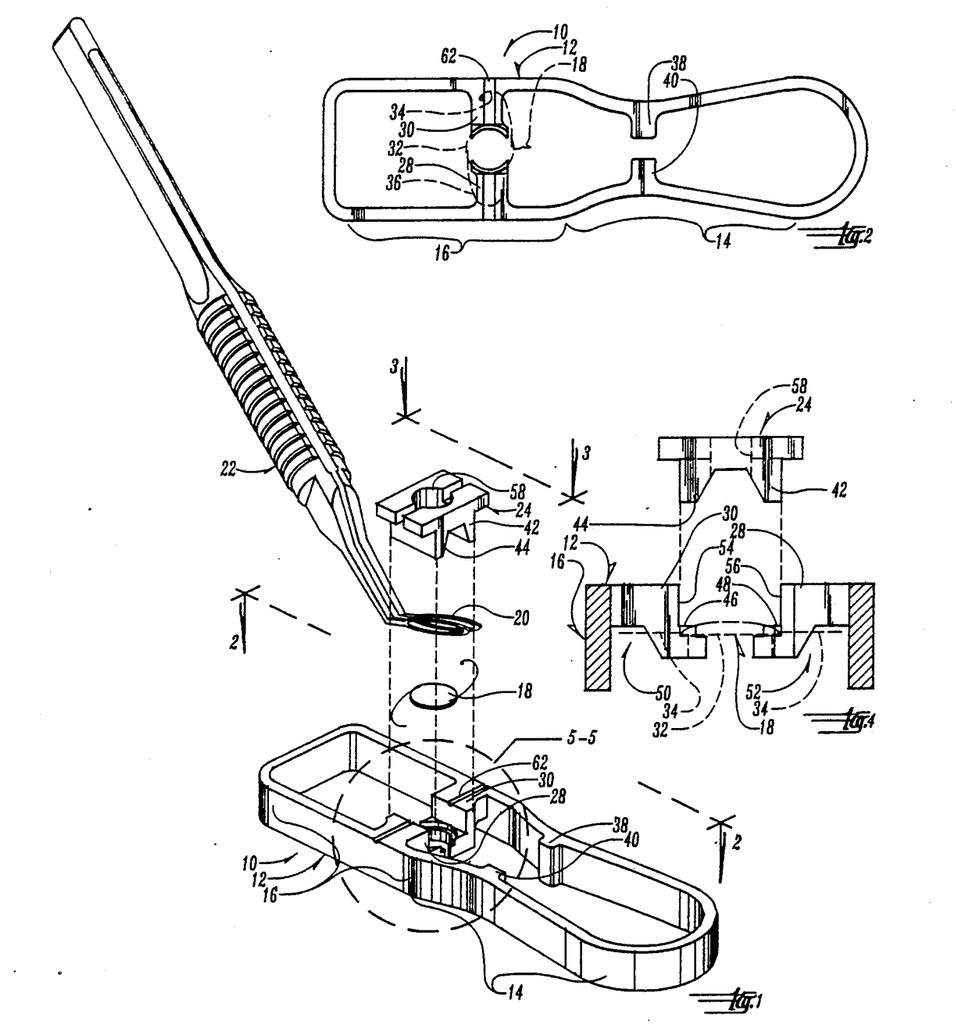
FIG. 1 is a perspective view of an embodiment according to the invention showing certain portions in an exploded fashion, and also illustrating an embodiment of a forceps which can be used with the invention.
FIG. 2 is a top plan view taken along line 2—2 of FIG. 1.
FIG. 4 is an enlarged sectional view taken along line 4—4 of FIG. 3 but showing the lens in a supported position.

FIG. 2 illustrates how the lens 18 can be placed on curved support jaws 28 and 30 at the supporting portion 16 of frame 12. In its normal position, the separation between the bottom lens supporting portions of jaws 28 and 30 is slightly less than the outside diameter of the optic portion of lens 18. The separation between the portions of jaws 28 and 30 hold the lens in position on opposite sides of the perimeter of the lens which is slightly greater than the diameter of the lens. (See FIG. 4). Note how the curvature of jaws 28 and 30 basically follows the curvature of the diameter of lens 18 (see FIG. 2). As will be described in more detail later, a portion of jaws 28 and 30, however, supports lens 18 underneath its perimeter, whereas another curved portion of jaws 28 and 30 abuts the perimeter or a portion of the perimeter of lens 18. This allows lens 18 to be held in position within jaws 28 and 30. The jaws 28 and 30 of supporting portion 16 basically cradle and support lens 18. It should be noted that it is supported only as to portions at or near the perimeter of lens 18. This reduces the risk of any damage to the center portion of lens 18. FIG. 2 also illustrates how the haptic portions 34 and 36 of lens 18 can be accommodated by the structure of frame 12. The sides of jaws 28 and 30 have cutout areas 50 and 52 that allow haptics 34 and 36 to enter unobstructed (as shown in FIG. 2 and 4). These areas 50 and 52 are cleared to allow space for the haptics when optic 32 is in position as shown in FIG. 4. This structure is also beneficial to the extent it helps hold the optic in position. Notice also how the stops 38 and 40 on the gripping portion 14 of frame 12 are somewhat separated. The stops 38 and 40 determine how far the opposite sides of gripping portion 14 can move towards one another when manual pressure is applied inwardly. As will be further described below, such manual pressure causes jaws 28 and 30 to move together which controls the folding process of lens 18.

Figure 3:
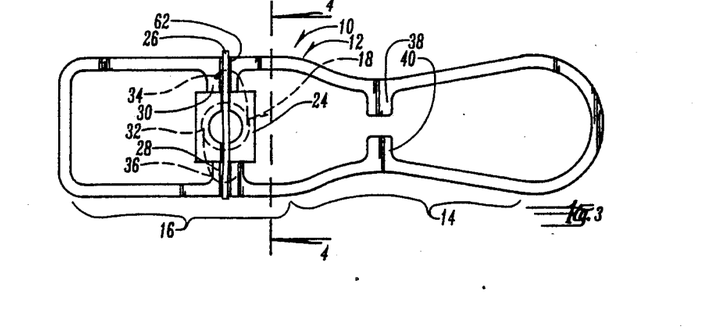
FIG. 3 is a top plan view taken along line 3—3 of FIG. 1 also illustrating the elements (except the forceps) assembled and the position of a rubber band or other means to hold the elements together for shipping, if desired.

FIG. 3 is similar to FIG. 2 except it shows how block insert 24 and lens 18 can be packaged and secured in supporting portion 16 of frame 12. Lower legs 42 and 44 of blocking insert 24 matingly insert into a space above support jaws 28 and 30, abutting vertical walls 54 and 56 of jaws 28 and 30 to prevent jaws 28 and 30 from moving towards one another which could damage or dislodge lens 18. Note also how block insert 24 includes circular opening 58 and spacing between legs 42 an 44 to avoid any potential damage to optic portion 32 of lens 18. Legs 42 and 44 prevent dislodging of the lens during shipping and handling. The center portion of optic 32 needs to be clear and free from abutment or abrasion with anything.

FIG. 4 shows in more detail the exact structure of supporting portion 16 of frame 12. In particular, it shows how lens 18 sits directly on top of curved support jaws 28 and 30. Furthermore, raised curved ledges 46 and 48 exist on top of support jaws 28 and 30. These ledges serve as stops when block insert 24 is inserted, so that block insert 24 does not abut or damage lens 28. As described above, ledges 46 and 48 also serve to cradle or above opposite portions of the perimeter of optic portion 32 of lens 18 to hold it in position. Note again how in the conventional normal position of frame 12, lens 18 is supported in its normal flat condition and absolutely no structure abuts or is adjacent to the top or bottom center portion of optic 32 of lens 18.

Figure 5:
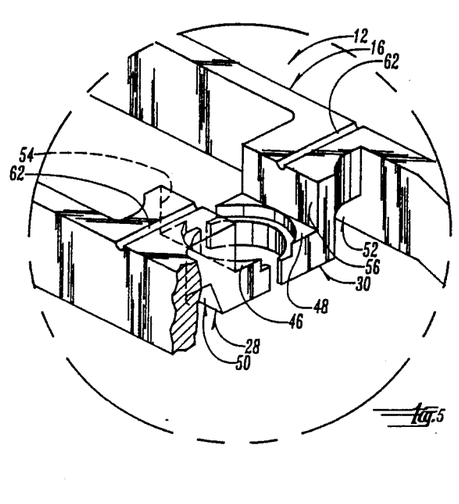
FIG. 5 is an enlarged sectional view and partial cutaway view taken along line 5—5 of FIG. 1.

FIG. 5 shows in more detail the exact structure of the supporting portion 16 of frame 12, in an enlarged fashion. It is noted that there is no supporting structure immediately beneath the center of lens 18 when supported. Also, there is no mandrel or other structure beneath lens 18 to assist folding of lens 18. This reduces risk of damage to lens 18 and distinguishes the present invention from some other lens folders. A better view of the curved nature of jaws 28 and 30, and raised ledges 46 and 48 can be seen. Also note that channels 60 and 62 can be utilized to guide and maintain a rubber band or other means around frame 12 if desired. A similar channel can exist on insert 24 to cooperate with a rubber band.

Figure 6A:
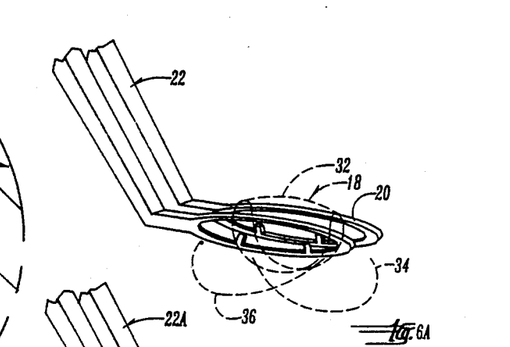
FIG. 6A is an enlarged perspective view illustrating the forceps tips of FIG. 1 gripping a folded intraocular lens.

Still further, FIG. 5 illustrates how jaws 28 and 30 support the lens in an intermediate position in frame 12, both from either side of frame 12, and from the top and bottom of frame 12. This further facilitates the easy and secure packaging and shipping of frame 12 with a lens 18 in place, and also makes it easy for the surgeon to use when ready to fold and grasp the lens during surgery. FIG. 6 illustrates tips 20, similar to those illustrated in FIG. 1, are unique in that they consist of an oval shaped frame 64 with an opening 66 in the middle. Teeth 68 extend from the bottom of oval shaped frame 64 upwardly at spaced apart locations of each tip 20. As shown in FIG. 6A, when the optic portion 32 of lens 18 is folded, portions of the folded lens 18 can expand into openings 66. This is especially true for the type of silicone lenses which tend to creep out from within the grasp of the forceps. The ability to conform and expand into opening 66 assists in insuring that the lens 18 can be reliably and accurately gripped and maintained in the accurately folded position. Still further, teeth 68, as optional features, can further this goal by providing assistance in gripping those portions of lens 18 that extend into opening 66.

FIG. 6A shows how a particular set of tips 20 of forceps 22 can be used to fold and grip a lens 18.

It is furthermore pointed out that tips 20 shown in FIG. 6A are configured to allow haptics 34 or 36 to be folded up inside tips 20, either through or between openings 66, or in other manners well within those ordinary skill in the art. Tips 20 could also include hooks, appendages, or other connection means for securing a haptic 34 or 36, if desired. This would facilitate the control of position of haptic 34 or 36 and prevent them from effecting the insertion process of lens 18 into the eye.

Figure 6B:
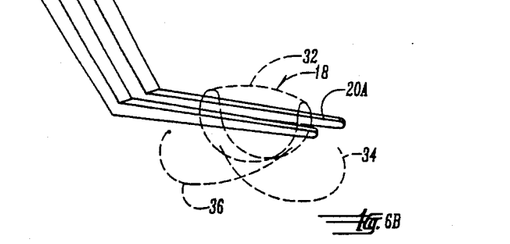
FIG. 6B is an enlarged perspective view of an alternative embodiment of forceps tips gripping a folded intraocular lens.

FIG. 6B illustrates a more generic set of tips 20A for forceps 22A. In this embodiment tips 20A are merely flat, elongated members which are angled with respect to the body of forceps 22A. Each tip 20A would be converged upon opposite sides of the folded lens 18 as can be well appreciated in the art. It is pointed out that the invention could be used with a variety of different forceps and forceps tips.

FIGS. 7–10 illustrate the operation of folder 10. Each of these figures illustrates a particular stage of the process of folding of lens 18. It is to be understood that the primary advantage of folder 10 is the ability to support lens 18 in the vice-like structure of jaws 28 and 30, which at the same time allows virtually automatic positioning of tips 28 of forceps 22 in this vice-like structure. Thereafter, it is only a matter of manually closing the jaws 28 and 30 of the vice-like structure of folder 10. As jaws 20 and 30 converge, the portions underneath lens 18, prevents lens 18 from moving downwardly, and the presence of forceps tips 20 on the perimeter edges of lens 18 causes lens 18 to fold upwardly inside the prepositioned forceps tips 20. The process continues until forceps tips are pushed together to the point where the lens, now accurately and reliably folded into the tips, can be reliably gripped and removed, ready for insertion into the eye.

Figure 7:
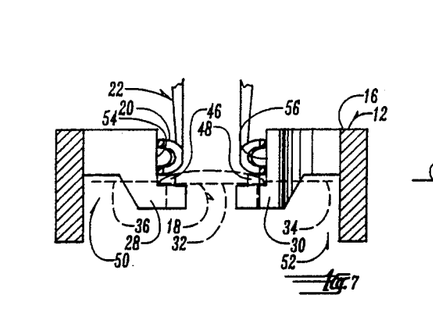
FIG. 7 is a sectional view generally similar to FIG. 4, but showing the normal position of an intraocular lens mounted on the invention, and the initial positioning of a forceps tips with respect to the lens. The shipping block 24 of FIG. 4 is completely removed in this FIG.

FIG. 7 is similar to FIG. 4, and shows how raised ledges 46 and 48 serve to automatically position tips 20 of forceps 22 immediately by the perimeter edge of the optic portion 32 of lens 18. This allows the surgeon to quickly and easily position the tips so that they will accurately and reliably grasp and remove the lens. There does not have to be any manual estimation or checking of positioning of the forceps tips 20.

Figure 8:
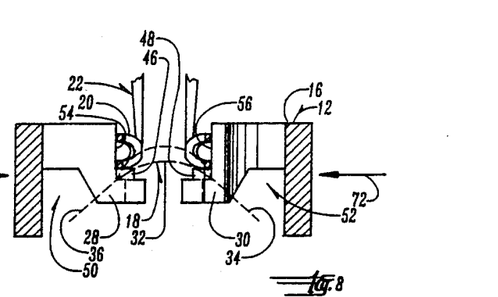
FIG. 8 is similar to FIG. 7 but shows how the invention operates to automatically begin reliable and accurate folding of the lens in the forceps tips.

FIG. 8 then shows that once tips 20 of forceps 22 are positioned, gripping portion 14 (see FIG. 1) is squeezed together to begin folding of lens 18 in tips 20. The movement of the opposite sides of gripping portion 14 in turn causes the movement of opposite sides of supporting portion 16 to cause support jaws 28 and 30 to move towards one another (illustrated by arrows 70 and 72). This automatically moves forceps tips 20 towards one another while causing the optic portion of lens 18 to bow and fold upwardly. It also automatically controls the position that forceps tips 20 will grasp the lens.

Figure 9:
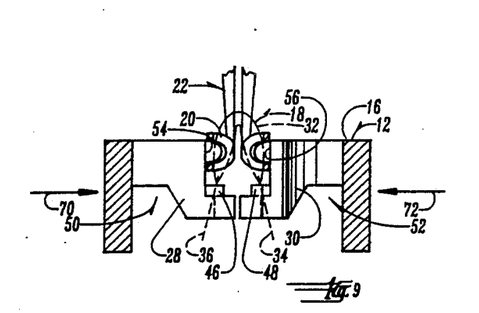
FIG. 9 is similar to FIG. 8 but shows completion of the automatic folding process of the lens in the forceps tips in the invention.

FIG. 9 shows the completion of movement of the opposite sides of supporting portion 16 towards one another and the correct and accurate gripping of the lens 18 above the perimeter edge of the optic 32. The forceps tips are then squeezed together prior to releasing pressure applied to portion 14.

Figure 10:
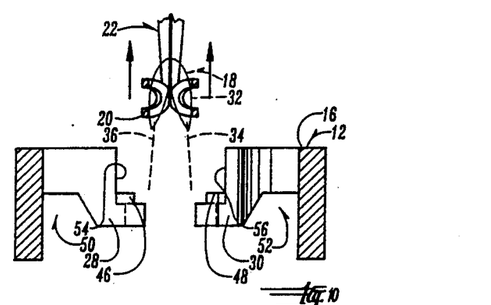
FIG. 10 is similar to FIG. 9 but shows how the lens, folded and gripped by the forceps tips, can be separated from the invention.

Finally, FIG. 10 shows that when the gripping portion 14 is released to allow the opposite sides to resiliently move apart (back to their normal position) from one another, the opposite parts of supporting portion 16 also move apart to allow the forceps tips to continue to reliably grip lens 18 and remove it from folder 10 for insertion into the eye during surgery.

The embodiment of FIGS. 1–10 can be made of a white polypropylene material. Optic portion 32 of lens 18 has a diameter of approximately 0.240 inches. The width of the portion of jaws 28 and 30 upon which lens 18 would be supported is approximately 0.02 inches.

Figures 11, 12:
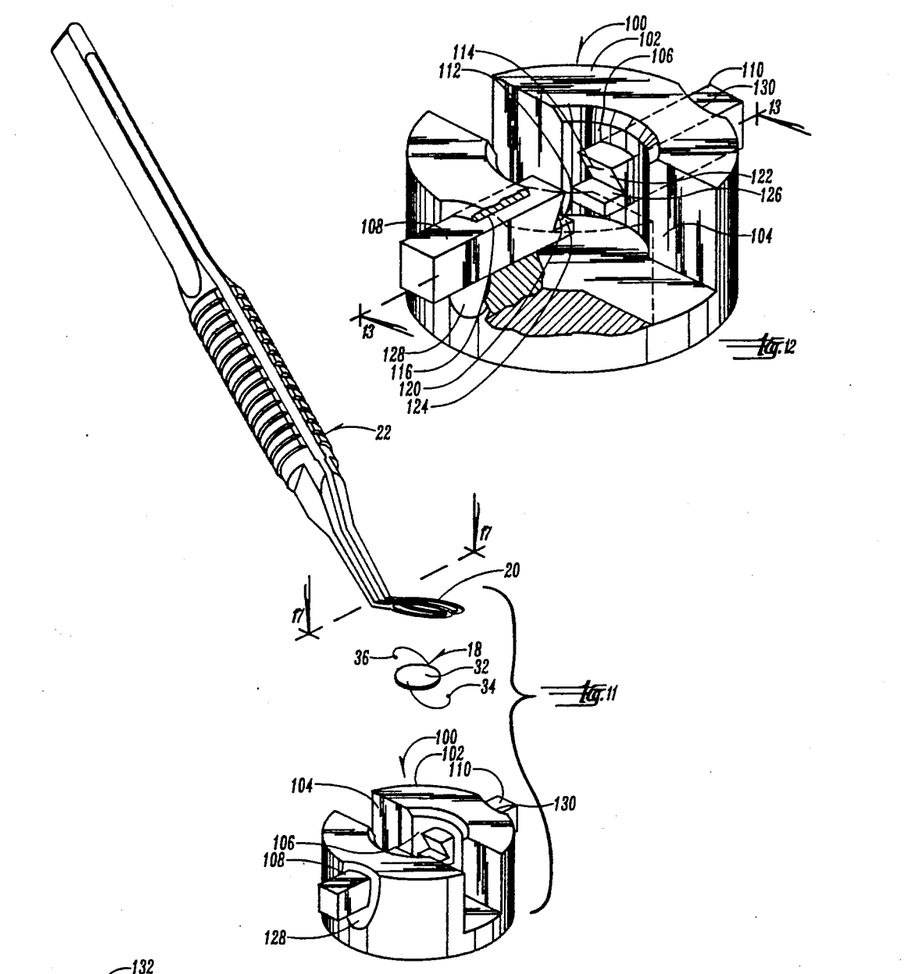
FIG. 11 is a perspective view of a second embodiment according to the present invention, showing in somewhat exploded fashion an intraocular lens and a forceps that can be used with the invention.
FIG. 12 is an enlarged perspective view and partial cutaway view of the invention shown in FIG. 11.

FIG. 11 shows a second embodiment of the present invention. Folder 100 comprises a base 102 of generally cylindrical shape but having a channel 104 generally bisecting base 102 laterally. A circular bore 106 exists through the center of base 102 along its vertical axis.

Folder 100 works very similarly to folder 10 previously described with respect to FIGS. 1–10 except it utilizes moveable arms 108 and 110 each having beveled or notched inner ends 112 and 114. The beveled inner ends 112 and 114 provide the support and positioning of lens 18 in holder 100. Arms 108 and 110 are mateably insertable and slideable through square bores 116 and 118 in base 102. The outer ends of arms 108 and 110 are always gripable and manually maneuverable by a user to allow the user to move one or both arms 108 and 110 towards and away from one another. FIG. 11 shows how a lens 18 can be moved and inserted between arms 108 and 110 by either setting it upon horizontal ledges 124 and 126 of beveled ends 112 and 114 from above, or sliding it in through channel 104 sideways onto ledges 124 and 126. The opening defined by channel 104 and bore 106 then allows tips 20 of forceps 22 to be inserted downwardly into folder 100 and automatically positioned as shown in FIG. 13.

FIG. 12 shows in more detail the relationship of arms 108 and 118 and base 102. In a normal position, arms 108 and 110 are separated a sufficient distance so that a lens 18 in its normal unfolded state can be placed on ledges 124 and 126. Additionally, arms 108 and 110 are positioned so that the opposite perimeter edge of lens 18 abuts against the beveled inner ends 112 and 114 at the junction of upwardly angled portions 120 and 122 with ledges 124 and 126 respectively (see FIG. 13). The beveled inner ends 112 and 114 therefore serve the dual purpose of supporting lens 18 and maintaining it in a secure position.

Note also that recesses 128 and 130 can be formed in the extra side wall of base 102 if desired to make gripping of the outer ends of arms 108 and 110 easier.

Figures 13, 14:
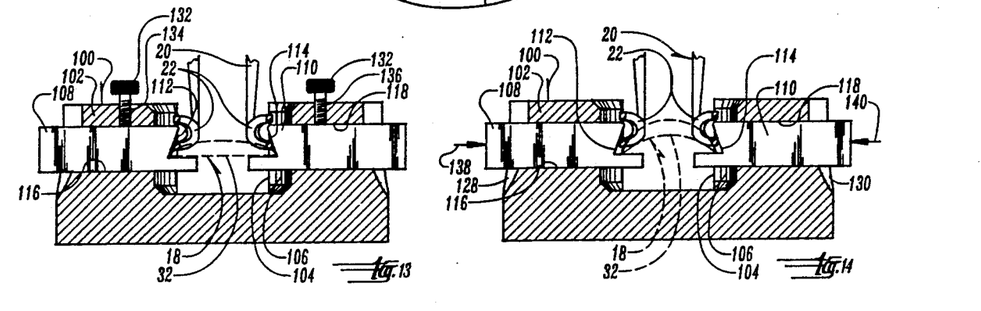
FIG. 13 is an enlarged sectional view taken along lines 13—13 of FIG. 12 additionally showing the intraocular lens positioned in the invention and the forceps tips in position prior to the beginning of the folding of the lens.
FIG. 14 is similar to FIG. 13 but shows the process of beginning the automatic folding of the lens within the forceps tips.

Turning to FIGS. 13–16, the sequence of steps for folding of the lens are shown. These are essentially similar to those shown at FIG. 7–10. In this case, however, either one arm 108 or 118, or both arms 108 and 118 can be moveable. As depicted in FIG. 13, set screws 132 and 134 could optionally be included to be threadably moveable in threaded bores 136 and 138 in the top of base 102 in alignment of arms 108 and 110. Set screws 132 and 134 could then be adjustable to either secure either arm 108 or 110 into a fixed position, or loosen to allow slideable, lateral movement. Set screws 132 and 134 are optional, and other types of securing means, either releaseable or not, could be utilized with the invention. Therefore, it is to be understood that either arm can be releasably secured in any linear position by means known in the art such as a set screw or some other device.

Figure 15:
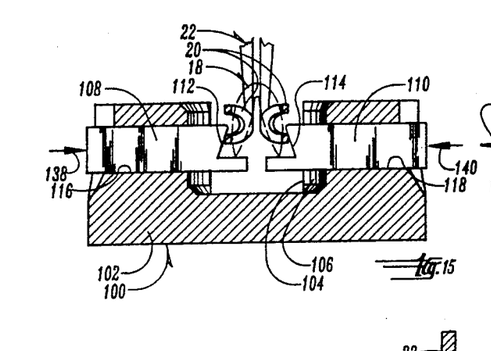
FIG. 15 is similar to FIG. 14 but showing the completion of folding of the lens within the forceps tips.
Figure 16:
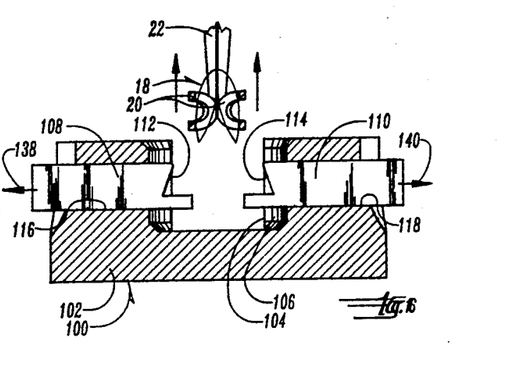
FIG. 16 is similar to FIG. 15 but showing the removal of the folded lens gripped within the forceps tips from the invention.
Figure 17:
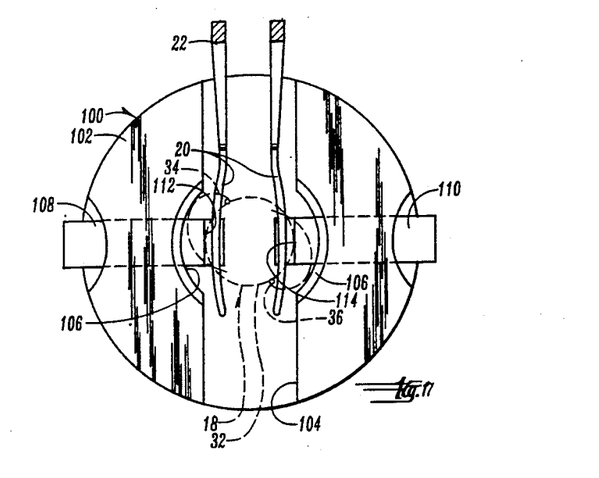
FIG. 17 is a top plan view taken generally along line 17—17 of FIG. 11.

It can be appreciated, the depictions in FIGS. 13–16 (as in FIGS. 7–10) illustrate forceps tips 22 of the particular type of forceps 20, where the tips 22 have the shape and configuration shown in more detail in FIG. 6A (see also FIG. 17). The cross sectional views of FIGS. 13–16 (and 6–10) show that the tips 22 are bowed or curved along a longitudinal axis. Therefore, in these figures, only the first portions of tips 22 which are diverging are seen. As can be more fully appreciated with reference to FIG. 17, these particular forceps tips 22 from a top view have an inside concave shape and an outside convex shape. It is to be clearly understood, however, that alternative types of forceps and forceps tips can be utilized as has been previously explained.

FIG. 14 illustrates that manual force against one or both of arms 108 and/or 110 inwardly (as indicated by arrows 138 or 140) will in turn move beveled inner ends 112 and/or 114 towards one another. Similarly to jaws 28 and 30 of folder 10 in FIG. 1, the forceps tips 22 are automatically positioned and the lens is folded within the tips automatically by this system. One difference between beveled inner ends 112 and 114 and jaws 28 and 30 is that the beveled inner ends 112 and 114 are not curved to mimic the perimeter of lens 18. However, as can be appreciated with reference to FIG. 18, the upward bowing of lens 18 when arms 108 and/or 110 is/are moved inwardly lifts the bottom surface of lens 118 so that there again is a reduced risk of any damage, abrasion, or abutment of the middle portion of optic 32 with the structure of folder 100.

FIG. 15 shows the further step of bringing arms 108 and 110 into further convergence accurately and automatically folding lens 18 within tips 22. FIG. 16 shows how arms 108 and 110 can then be retracted and the forceps can be raised from folder 100 with the accurately folded lens particularly gripped in tips 22.

FIG. 17 shows the top plan view of folder 100. It further illustrates how forceps tips 20 are automatically positioned with respect to optic 32 by the configuration of beveled inner ends of 112 and 114 or arms 108 and 110 when they are in what is called their "normal" position supporting lens 18 in its unfolded stated. Note further how the curved segments of bore 106 allow haptics 34 and 36 to be positioned under supporting arms 108 and 110 in generally normal position when lens 18 is supported in an unfolded state on folder 100. Note also that the beveled inner ends 112 and 114 only support a relatively small portion near the perimeter of optic 32. Channel 104 basically steers the forceps 22 into a position perpendicular to arms 108 and 110. By referring back to FIG. 13-16, it can also be seen that a space exists underneath inner beveled ends 112 and 114 to accomodate the haptics without damage during storage and folding.

Folder 100 can be made of a variety of different materials. For example, base 102 can be made of a variety of different types of plastics, as can arms 108 and 110. Arms 108 and 110 can alternatively be made of metal or other materials if desired.

Figure 18:
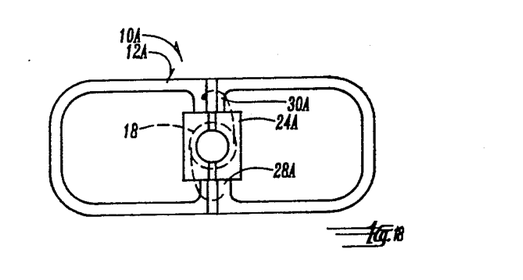
FIG. 18 is a top plan view of a third embodiment according to the present invention.

FIG. 18 shows a still different embodiment of the invention. The folder 10A is quite similar to folder 10. In fact, its supports jaws 28A and 30A are exactly the same as jaws 28 and 30 of folder 10. Lens 18 is supported and folded in exactly the same manner because of this identity of structure. Additionally, a block insert 24A can be used for storage and/or packaging and/or shipping, as explained with regard to folder 10.

The major difference between folder 10A and folder 10 is the configuration of frame 12A (except for jaws 28A and 30A). Instead of having an explicit gripping portion 14 and supporting portion 16, as described with respect to folder 10, folder 10A basically has an oval shaped outer frame with the jaws 28A and 30A extending inwardly towards each other at the center of this frame. The resilient nature of frame 12A would allow the user to basically push the sides of frame 12A together in line with jaws 28 and 30 on opposite sides to allow the jaws 28A and 30A to move towards each other once block insert 24A is removed. This embodiment represents a more simplified version but one which still would adequately protect lens 18 from all sides, when block insert 24A is used and the entire folder 10A is boxed or packaged for shipment.

It can therefore be seen that the invention achieves at least all of its stated objectives. It will be appreciated that the present invention can take many forms in embodiments. The true essence and spirit of this invention are defined in the appended claims, and it is not intended that the embodiment of the invention herein should limit the scope thereof.

The invention presents a lens folding device which is economical, from a variety of standpoints, including but not limited to manufacturing, packaging, and use. Its economical nature can allow it to be packaged with individual lenses so that all the surgeon has to do is open the sterilized package, remove any block inserts or other packaging materials, automatically have the lens folded within the forceps tips, and throw the folder away. Alternatively, of course, the folder could be reutilized if sterilized.

The folder is relatively small in size, has few critical tolerances and moving parts, if any depending upon the embodiment, and improves the ability of the surgeon to quickly but accurately and reliably fold and grasp a foldable intraocular lens. The invention basically operates as an automatic forceps tips positioner with respect to the lens and then as a vise which automatically maintains the accurate gripping position of the forceps tips while the lens is folded within them. It eliminates the surgeon having to manually estimate the correct gripping location or having to utilize two forceps or other instruments to assist in the folding process.

What is claimed:

1. A means for facilitating folding of an intraocular lens, having a lens optic to prepare the lens for insertion through a small incision in the eye, comprising: a base means;

translateable supporting means associated with the base means for supporting at least a portion of the perimeter of a lens optic;

positioning means associated with the supporting means generally for receiving and positioning opposite tips of a forceps near opposite sides of the perimeter of the lens optic when the lens optic is supported on the supporting means;

manually moveable means associated with the base means for translateably moving the supporting and positioning means towards one another, folding the lens optic within the forceps tips while simultaneously maintaining the forceps tips in a desired position to the lens optic as the lens optic is folded.

2. The means of claim 1 wherein the supporting and positioning means comprises curved jaws adapted to be adjacent to opposite diametric sides of the optic, and the manually moveable means comprises extension means for allowing mechanical force to be transferred to the curved jaws to converge the forceps tips towards one another to allow the opposite sides of the lens optic to be folded onto one another and the forceps tips to grip the lens optic at a desired position.

3. The means of claim 1 wherein the extension means of the manually moveable means comprises rigid frame members connected to the base, which is comprised of resilient frame members, so that manual inward pressure on the resilient frame members of the base causes convergence of the rigid frame members which in turn causes folding of the lens optic within the forceps tips.

4. The means of claim 1 wherein the manually moveable means comprises moveable members within the base means to simultaneously push opposite sides of the lens towards one another as forceps tips are closing upon one another to fold the lens optic within the forceps tips.

5. The means of claim 1 further including an intraocular lens optic received in the supporting means, the optic being a plano-convex member.

6. The means of claim 1 further including an intraocular lens optic received in the supporting means, the optic being foldable.

7. The means of claim 6 further including an intraocular lens optic received in the supporting means, the optic being soft.

8. The means of claim 7 further including an intraocular lens optic received in the supporting means, the optic being made of silicone.

9. The means of claim 7 further including an intraocular lens optic received in the supporting means, the optic being made of a plastic material.

10. A means for folding a soft intraocular lens wherein the lens is folded within forceps tips that are then used to insert the lens into the eye, comprising: a base means;

opposite jaw means associated with said base means including: first means to position and hold a lens, and second means to allow insertion of and to position the forceps tips with respect to a desired position on top of the lens near opposite diametrical sides of the lens when the lens is positioned in the first means; and manually moveable means connected to the jaw means to manually converge the jaw means to guide the forceps tips with respect to the lens as it is being folded in the forceps tips by movement of the jaw means toward one another.

11. The means of claim 10 wherein the manually moveable means are integrally connected and formed with the base means, and the base means has at least portions which are resilient to allow manual movement of the resilient portion of the base means to move the jaw means.

12. The means of claim 10 wherein the first means of the opposite jaw means comprises a stepped and curved portion which can position and support a portion of the bottom perimeter of the optic of a lens.

13. The means of claim 10 wherein the second means comprises a raised member from the first means to provide a landing for the vertical insertion of forceps tips to an area adapted to be adjacent opposite diametrical portions of the top of a optic portion of a lens when the lens is positioned in the first means.

14. The means of claim 10 wherein the first and second means are curved to conform generally to curvature of an optic portion of the lens.

15. The means of claim 10 wherein the first and second means are flat surfaces.

16. The means of claim 10 wherein the manually moveable means are independent arms extending through bore in the base means along an axis, the arms moving the jaw means when manually moved along an axis.

17. A device for folding a soft intraocular lens within forceps comprising:

a frame means including a closed resilient rail means defining an interior area, and aligned inwardly extending arms connecting to the rail means;

spaced apart jaw members positioned at the facing ends of the arms including, first curved inwardly extending ledges means for supporting opposite bottom portions of a lens near the perimeter of the lens;

second concentric curved ledge means positioned on top of the first curled ledge means and extending inwardly but less than the first curved ledge means for abutting opposite portions of the perimeter of the lens and providing a landing for placement of forceps tips;

the spacing between jaw members being such that in a first normal position the diametrical distance between opposite first curved ledge means is less than the diameter of the lens, the diametrical distance between opposite second curved ledge means being slightly greater than the diameter of the lens, and converging movement, of the jaw members urging a less received between the jaw member to fold upwardly along a center axis which is generally perpendicular to an axis between jaw members and midway between jaw members, the converging movement also folding the lens within the forceps tips.

18. The device of claim 17 wherein the frame means is made of a plastic material.

19. The device of claim 17 wherein the first and second curved ledge means have radii of curvature which are generally similar to the radii of curvature of the optic portion of the lens.

20. A means of folding an optic portion of a soft intraocular lens along a first axis formed by a diameter of the lens, comprising:

a base means having top, bottom, and opposite side walls;

an opening extending through the top wall to receive a lens within the base means;

said opposite arms moveable positioned within bores through opposite side walls of the base means along a second axis;

inner ends of the arms being moveable towards one another within the opening in the base means; jaw member configured on each inner end of the arms, the jaw member including a flat and inwardly extending horizontal surface and an upwardly angled surface form the horizontal surface forming an acute angle with the horizontal surface;

the horizontal surface being adapted to support opposite bottom portions of the perimeter of the optic when the arms are in a first position, the angled surface being adapted to hold the lens in place generally along said second axis and accurately position the forceps tips with respect to the lens when the arms are in the first position;

convergence of the jaw members by manual movement of one or more of the arms causing accurate upward folding of the lens within the forceps tips, divergence of the jaws allowing removal of the forceps tips gripping the folded optic.

21. A method of folding an optic portion of a soft intraocular lens along a fold line coincident with a diameter of the optic, comprising the steps of:

supporting opposite bottom, perimeter portions of the optic;

bringing jaw structures into abutment with the perimeter of the optic;

moving tips of a forceps within the jaws adjacent to the optic near the abutment of the jaw structure with the optic to accurately position the tips prior to folding of the lens; converging the jaw structures to guide the forceps tips and concurrently fold the optic within the forceps tips so that the optic is gripped thereby;

diverging the jaw structures to enable removal of the forceps tips while the tips are gripping the folded optic.

* * * * *